(12) United States Patent
Tomisek et al.

(10) Patent No.: US 8,213,001 B2
(45) Date of Patent: Jul. 3, 2012

(54) METHOD AND APPARATUS FOR DETECTING MICROSCOPE SLIDE COVERSLIPS

(75) Inventors: John D. Tomisek, Lombard, IL (US);
Robert W. Jaekel, Deer Park, IL (US);
Ronald E. Kukla, Wheeling, IL (US);
Russell L. Sage, McHenry, IL (US);
Shahin Iqbal, Rochester Hills, MI (US)

(73) Assignee: Abbott Laboratories, Des Plaines, IL (US)

( * ) Notice: Subject to any disclaimer, the term of this patent is extended or adjusted under 35 U.S.C. 154(b) by 191 days.

(21) Appl. No.: 12/653,905

(22) Filed: Dec. 18, 2009

(65) Prior Publication Data

US 2010/0165326 A1 Jul. 1, 2010

Related U.S. Application Data

(60) Provisional application No. 61/203,130, filed on Dec. 19, 2008.

(51) Int. Cl.
*G01J 3/00* (2006.01)
(52) U.S. Cl. ............................ 356/51; 356/213; 356/218
(58) Field of Classification Search ........................ None
See application file for complete search history.

(56) References Cited

U.S. PATENT DOCUMENTS

| | | | |
|---|---|---|---|
| 4,922,112 A | 5/1990 | Zierl et al. | 250/372 |
| 5,566,249 A * | 10/1996 | Rosenlof et al. | 382/257 |
| 5,638,459 A * | 6/1997 | Rosenlof et al. | 382/133 |
| 5,812,692 A * | 9/1998 | Rosenlof et al. | 382/133 |
| 6,796,353 B2 | 9/2004 | Lang et al. | 156/556 |
| 2003/0047863 A1 | 3/2003 | Lang et al. | |
| 2005/0156046 A1* | 7/2005 | Goldenberg | 235/462.13 |
| 2009/0129660 A1* | 5/2009 | Gregson | 382/133 |

FOREIGN PATENT DOCUMENTS

| | | |
|---|---|---|
| EP | 1 526 384 A2 | 4/2005 |
| GB | 2 107 680 A | 5/1983 |
| JP | 08 334444 A | 12/1996 |
| JP | 2001 337280 A | 12/2001 |
| WO | WO 2008/046593 A2 | 4/2008 |

OTHER PUBLICATIONS

International Search Report for PCT Application No. PCT/US2009/006638.
Written Opinion for PCT Application No. PCT/US2009/006638.

* cited by examiner

*Primary Examiner* — Michael P Stafira
(74) *Attorney, Agent, or Firm* — McDermott Will & Emery LLP

(57) ABSTRACT

A method and apparatus of the present invention determines whether zero, one, or a plurality of microscope slide coverslips are about to be applied to a microscope slide. Light, such as ultraviolet light, may be directed toward a coverslip testing region, in which a number of coverslips reside. The amount of light passing through the coverslip testing region is collected and measured. Based on the measured amount, the method and apparatus determine the number of coverslips present in the coverslip testing region.

21 Claims, 5 Drawing Sheets

METHOD AND APPARATUS FOR DETECTING MICROSCOPE SLIDE COVERSLIPS

RELATED APPLICATIONS

This application claims priority to U.S. Provisional Patent Application Ser. No. 61/203,130 filed Dec. 19, 2008, which is expressly incorporated herein by reference.

TECHNICAL FIELD

The present invention relates generally to a method and apparatus for detecting microscope slide coverslips. More particularly, the present invention relates to a method and apparatus for discerning between a number of microscope slide coverslips, including discerning between zero, one, and a plurality of microscope slide coverslips. The invention may be implemented as a stand-alone apparatus, or in an automated slide staining system for preparing microscope slides for analysis. Furthermore, the invention may be implemented in an automated coverslip application and removal apparatus or system. The present invention may also be implemented in an automated analyzer, for example, an automated diagnostic analyzer.

BACKGROUND

In an automated microscope slide staining system, such as, for example, the commercially available Xmatrx™ Automated Slide Staining System from Abbott Molecular, Des Plaines, Ill., and BioGenex Laboratories, Inc., San Ramon, Calif., microscope slide coverslips are automatically applied to and removed from a microscope slide having a biological sample thereon. The coverslips are applied to and removed from the microscope slides during processing of samples, such as processing that prepares samples for analysis, such as, for example, diagnostic analysis. During processing, such as, for example, washing, pretreatment, digestion, dehydration, deparaffinization, denaturation, hybridization, probe application, or reagent addition, the system expects that a single coverslip will be applied to the microscope slide each time a coverslip is applied to the slide, such as, for example, before hybridization or at the end of processing of the slide, such as prior to examination or analysis of the sample. However, coverslips have a tendency to stick together due to, for example, static forces or moisture existing between coverslips. Upon application of a plurality of coverslips to a microscope slide, subsequent removal of the coverslips from the microscope slide can leave at least one coverslip behind on the microscope slide. A bottom coverslip can be left behind on the microscope slide because the attraction between the bottom coverslip and the sample held on the slide is greater than the attraction between the bottom coverslip and the top coverslip or coverslips. As a result, additional sample processing is disrupted because the bottom coverslip left behind prevents access to the sample, which remains protected and covered by the bottom coverslip. Furthermore, coverslips sticking together could also result in loss of the additional coverslips into the automated system during transfer of the coverslips to and from the microscope slide, which could result in damage to the automated system.

Optical detectors are known which detect a plurality of microscope slide coverslips by optical reflectance. The optical detectors direct visible light toward the coverslips and detect the amount of light reflected back from the coverslips in order to determine the presence of a plurality of coverslips. The basis of this method appears to be measurement of the height or distance of the coverslips from the optical detector. Accordingly, the distance of a single coverslip from the detector is greater than the distance of a plurality of coverslips. The difference allows the detector to determine whether one, two, or more coverslips are present.

However, problems associated with this method are that the coverslips, themselves, are of relatively thin dimension such that the difference in thickness between a single coverslip and a plurality of coverslips, especially two coverslips, is small. For example, conventional coverslips vary in thicknesses between about 0.06 to about 0.25 millimeters. Thus, it is difficult to distinguish between a single coverslip and a plurality of coverslips using optical reflectance because the measured difference in distance between a single coverslip and a plurality of coverslips from the optical detector is small. Additionally, the optical reflectance method requires precise rotational and translational alignment of the coverslip to the optical detector. Because the difference in thickness between a single coverslip and a plurality of coverslips is small, a disruption in the alignment of the coverslip to the optical detection device may be equal to or greater than the difference in thickness between a single coverslip and a plurality of coverslips. Additionally, wear of a coverslip transfer mechanism which positions the coverslips at the optical detector may create inaccurate positioning of the coverslips at the optical detector over time. Thus, wear of the coverslip transfer mechanism may also lead to inaccurate measurements of the amount of light reflected resulting in inaccurate detection of a single coverslip or a plurality of coverslips. Furthermore, the optical detector may fade over time, due to, for example, the optical source fading, dirt or other material accumulating on the optical detection device, or corrosion of the optical detection device as it is exposed to processing chemicals and biological samples. Fading of the optical source may lead to diminished intensities of light over time, which will lead to inaccurate measurements of the amount of light reflecting back to the optical detector, resulting in an inaccurate detection of a single coverslip or a plurality of coverslips. Therefore, in view of the difficulties that result from utilizing an optical detection device, there is a need for an improved method and apparatus for detecting the number of microscope slide coverslips. Furthermore, there is a need for an improved method and apparatus for discerning between zero, one, and a plurality of microscope slide coverslips.

The present invention is provided to solve the problems discussed above and other problems, and to provide advantages and aspects not previously provided. A full discussion of the features and advantages of the present invention is deferred to the following detailed description, which proceeds with reference to the accompanying drawings.

SUMMARY

The teachings herein alleviate one or more of the above noted problems by providing a method and apparatus for discerning a number of microscope slide coverslips.

Such a method includes the step of directing light toward a coverslip testing region. The light is directed to pass through at least a portion of the coverslip testing region. The method also includes the step of discerning the number of coverslips in the coverslip testing region based on the amount of light passing through the coverslip testing region. The discerning step may include measuring a reduction of light passing through the coverslip testing region. In one embodiment, the method includes directing ultraviolet light at a wavelength of between about 200 and about 400 nanometers. The ultraviolet light may preferably be at a wavelength of between about 310 and about 320 nanometers. The amount of ultraviolet light passing through the coverslip testing region when zero coverslips are present in the coverslip testing region is about 100 percent of the light directed toward the coverslip testing region. In the example in which the wavelength of light is between about 310 and about 320 nanometers, the amount of ultraviolet light passing through the coverslip testing region when a single coverslip is present in the coverslip testing region is between about 40 and about 45 percent of the ultraviolet light directed toward the coverslip testing region, and the amount of ultraviolet light passing through the coverslip testing region when two coverslips are present in the coverslip testing region is between about 20 and about 25 percent of the ultraviolet light directed toward the coverslip testing region. Moreover, different ranges and values of the amount and wavelengths of light directed toward the coverslip testing region, and different ranges and values of the amount of light passing through a single coverslip or plurality of coverslips in the coverslip testing region are envisioned and within the scope of the present invention.

In another example, the method includes bringing a number of coverslips into proximity with a coverslip detection station which comprises an ultraviolet light source and an ultraviolet light detector. The number of coverslips are placed in the coverslip testing region formed between the ultraviolet light source and the ultraviolet light detector. The method also includes directing ultraviolet light from the ultraviolet light source toward the ultraviolet light detector in a path that travels through at least a portion of the coverslip testing region. In a further example, the method includes directing light from a light source toward the coverslip testing region. The method also includes the steps of directing light from a light source toward the coverslip testing region and determining the presence or absence of the number of coverslips in the coverslip testing region based on an amount of light reflected from the coverslip testing region and received by a light detector.

In another aspect of the invention, an apparatus includes an ultraviolet light source for producing ultraviolet light, an ultraviolet light detector for detecting ultraviolet light from the ultraviolet light source, and a transfer mechanism for bringing a number of coverslips into proximity with the ultraviolet light source and ultraviolet light detector. The ultraviolet light source directs ultraviolet light through at least a portion of a coverslip testing region. The ultraviolet detector detects ultraviolet light passing through the coverslip testing region to discern the number of coverslips in the coverslip testing region.

In another example, the apparatus includes a light source configured to direct light toward the coverslip testing region, and a light detector configured to detect light from the light source reflected from the coverslip testing region for determining the presence or absence of the number of coverslips in the coverslip testing region.

In another embodiment, an apparatus includes a coverslip detection station for discerning a number of coverslips. The coverslip detection station directs ultraviolet light through at least a portion of a coverslip testing region and discerns the number of coverslips in the coverslip testing region based on the amount of ultraviolet light passing through the coverslip testing region.

The apparatus may further include a transfer mechanism for bringing the number of coverslips into proximity with the coverslip detection station. In one example, the transfer mechanism brings the number of coverslips into the coverslip testing region between an ultraviolet light source and an ultraviolet detector by movement through a single plane extending between the ultraviolet light source and the ultraviolet detector. In another example, the transfer mechanism moves the number of coverslips to and from the coverslip detection station or the ultraviolet light source and ultraviolet light detector. In a further example, a coverslip stage moves to receive a number of coverslips and positions the number of coverslips in proximity to the light source and light detector. In yet another example, the coverslip detection station or the ultraviolet light source and ultraviolet light detector move toward and away from the number of coverslips. In still another example, the transfer mechanism moves the number of coverslips, and the coverslip detection station also moves to position both the coverslip detection station and the number of coverslips into and out of proximity with one another.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF DRAWINGS

The drawing figures depict one or more examples in accord with the present teachings, by way of example only, not by way of limitation. In the figures, like reference numerals refer to the same or similar elements.

DETAILED DESCRIPTION

Figure 1:
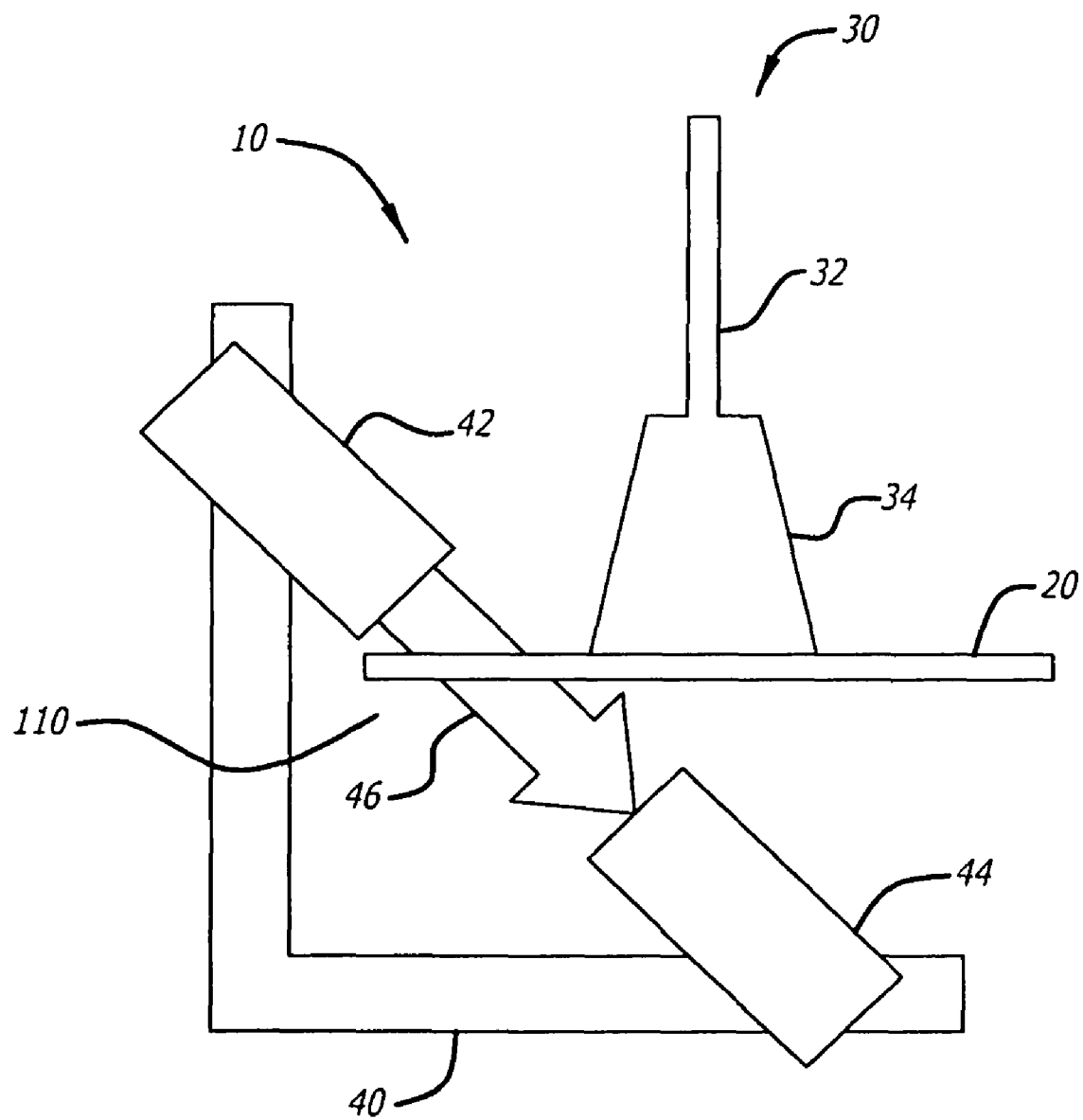
FIG. 1 is a front elevation of a microscope slide coverslip detection station according to an embodiment of the present invention.
Figure 2:
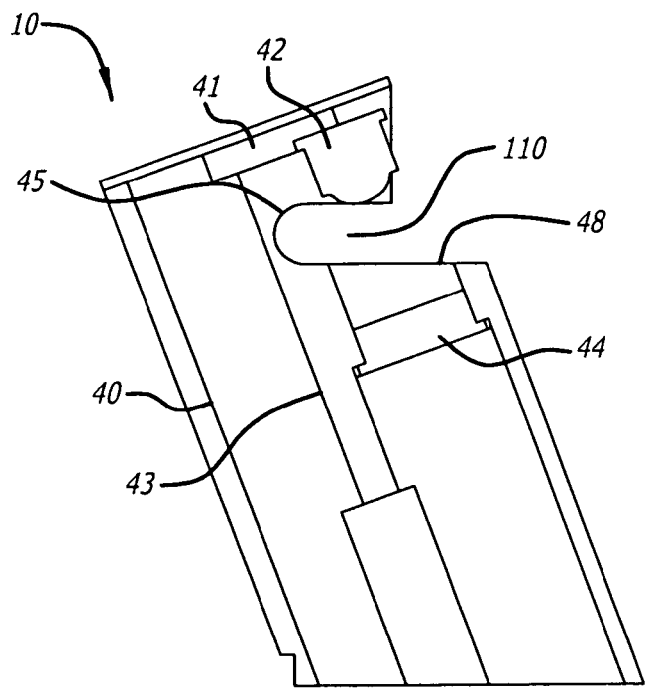
FIG. 2 is a cross section of a coverslip detection station according to another embodiment of the present invention

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The invention contemplates a method of discerning a number of microscope slide coverslips, including discerning between zero, one, and a plurality of microscope slide coverslips. In one embodiment, light is directed toward a coverslip testing region, such that the light will pass through at least a portion of the coverslip testing region. When a number of coverslips are actually present in the coverslip testing region, the light directed toward the coverslip testing region will also pass through at least a portion of the coverslips. In addition, when the number of coverslips in the coverslip testing region is zero, the light directed toward the coverslip testing region does not pass through a coverslip because no coverslips are present in the testing region. The amount of light which passes through the coverslip testing region is measured to discern the number of coverslips present in the coverslip testing region. This measured amount is compared with an amount of light that would result when no coverslip is present, for example, a calibration amount. The measured amount indicates whether zero, one or a plurality of coverslips are present in the coverslip testing region. When coverslips are actually present in the coverslip testing region, the measured amount is less than the calibration amount due to the coverslips absorbing a fraction of the light directed through the coverslip testing region.

In one example, the wavelengths of light directed toward the coverslip testing region extend from the near ultraviolet wavelengths to the far ultraviolet wavelengths. In another example, the wavelength of ultraviolet light may be between about 200 nanometers to about 400 nanometers. In a further example, the wavelength of ultraviolet light is between about 310 and about 320 nanometers. In the example of coverslips made of glass, a portion of ultraviolet light passing through a glass coverslip is absorbed by the coverslip. Thus, the amount of light passing through and exiting a coverslip is reduced by an amount that may be measured. In addition, the amount of light passing through and exiting a plurality of coverslips, for example two coverslips, is further reduced by a greater amount that may also be measured. As a result, the difference in the amount of light passing through a single coverslip and a plurality of coverslips is such that a measurable difference exists. This difference allows the discernment of the number of coverslips in the coverslip testing region, which may discern whether zero, one, or a plurality of coverslips are present in the coverslip testing region. The measurable difference exists, in part, because each coverslip absorbs about the same amount of light. Thus, the amount of light absorbed by one coverslip will be about half the amount of light absorbed by two coverslips, or in other words, two coverslips absorb about twice the amount of light than one coverslip.

In one embodiment, ultraviolet light at a wavelength of between about 310 and 320 nanometers is directed toward the coverslip testing region and passes through at least a portion of the coverslip testing region. Subsequently, the amount of ultraviolet light passing through the coverslip testing region is measured to discern the number of coverslips present in the coverslip testing region. Specifically, the presence of zero coverslips, a single coverslip or a plurality of coverslips may be determined. The amount of light passing through the coverslip testing region when no coverslips are present is about 100 percent of the light directed toward the coverslip testing region. In the example in which the wavelength of light is between about 310 and about 320 nanometers, the amount of light passing through a single coverslip in the coverslip testing region is between about 40 and about 45 percent of the amount of light directed toward the coverslip testing region. The measured amount of light passing through two coverslips in the coverslip testing region is between about 20 and about 25 percent of the amount of light directed toward the coverslip testing region. It will be understood that the measured amount of light passing through one coverslip will be greater than the measured amount of light passing through a plurality of coverslips, due to each coverslip absorbing substantially the same amount of light. In addition, it will be understood that the method of the invention also contemplates distinguishing between two, three, four, five or more coverslips. Also, it will be understood that other wavelengths of light may be used to discern the number of coverslips in the coverslip testing region, and therefore other values or percentages, or ranges of values or percentages, may result which are used to discern the number of coverslips in the coverslip testing region without departing from the spirit and scope of the invention.

It will be understood that coverslips of various materials and thicknesses absorb different amounts of light at different wavelengths of light. It will also be understood that in addition to different wavelengths of ultraviolet light, different ranges of other wavelengths of light may be used in accordance with the present invention, based on the material used for the coverslips, so long as the light travels substantially through the thickness of the coverslips when present in the coverslip testing region, without departing from the spirit and scope of the present invention.

The method of the invention is conveniently utilized with an apparatus for automatically discerning a number of microscope slide coverslips. The apparatus can include a station for discerning the number of coverslips at the station, however many coverslips may be present. Reference now is made in detail to the examples illustrated in the accompanying drawings and discussed below. It will be understood that similarly numbered components amongst the figures will refer to similar components, and the embodiments and examples of the various functionalities of such components will be consistent and similar and apparent to one of ordinary skill in the art.

Referring to FIGS. 1-8, examples of a coverslip detection station 10 are shown for discerning the number of microscope slide coverslips present within a coverslip testing region 110. A number of microscope slide coverslips 20 may be positioned in proximity with the coverslip detection station 10 and be positioned within the coverslip testing region 110 by a transfer mechanism 30. The coverslip detection station 10 includes a base 40, which includes a light source 42 and a light detector 44.

When ultraviolet light is used, the ultraviolet light source 42 may be an ultraviolet light-emitting diode, or other suitable device for emitting wavelengths of ultraviolet light. An example of light-emitting diodes suitable for the present disclosure are UVTOP® ultraviolet light-emitting diodes manufactured by Sensor Electronic Technology, Inc. which have peak emission wavelengths in the range of about 240 to about 400 nanometers. In another example, light source 42 may include a focusing lens (not shown) to focus the spot size of the light generated by the light source 42. The ultraviolet light detector 44 may be a photodiode, or other suitable device for receiving light. An example of a photodiode suitable for the present disclosure is a quartz windowed UV sensitive photodiode manufactured by Hamamatsu Photonics K.K. In another example, the light detector may be configured to sense narrow or predetermined wavelengths of light to provide greater resistance to background light being detected by the light detector 42. In a further example, apertures may be provided on the light source 42 and/or the light detector 44. The apertures function to shield the light source 42 and/or light detector 44 from background light or ambient light such that the amount of light received by the light detector 44 is substantially only that light produced by the light source 42.

The light source 42 and light detector 44 are positioned on the base 40 such that light emitted by light source 42 may be received by light detector 44, as indicated by arrow 46 in FIG. 1. The light source 42 and light detector 44 are configured so that light, such as ultraviolet light, directed toward the coverslip testing region 110 and passing through the coverslip testing region 110 is received by the light detector 44. As shown in FIGS. 1-5, light source 42 is above light detector 44, but the opposite configuration is also contemplated by the invention, i.e., the light detector 44 above the light source 42, as shown, for example, in FIG. 8.

As shown in FIGS. 2-5, the body 40 includes an upper arm 41 which houses the light source 42, and a lower portion 43 which houses light detector 44. The upper arm 41 extends only partially over the lower portion 43 in order to accommodate and at least partially receive, for example, a transfer mechanism 30. A cut-out 45 is formed in the body 40 between the upper arm 41 and lower portion 43. The cut-out 45 is formed to accommodate and receive at least a portion of a transfer mechanism, for example, holding thereon a number of coverslips 20. The cut-out portion includes the coverslip testing region 110 formed between the light source 42 and light detector 44. An aperture 48 is formed in the lower portion 43 to allow light generated by the light source 42 and directed toward the coverslip testing region 110 to be detected and received by the light detector 44.

Figure 8:
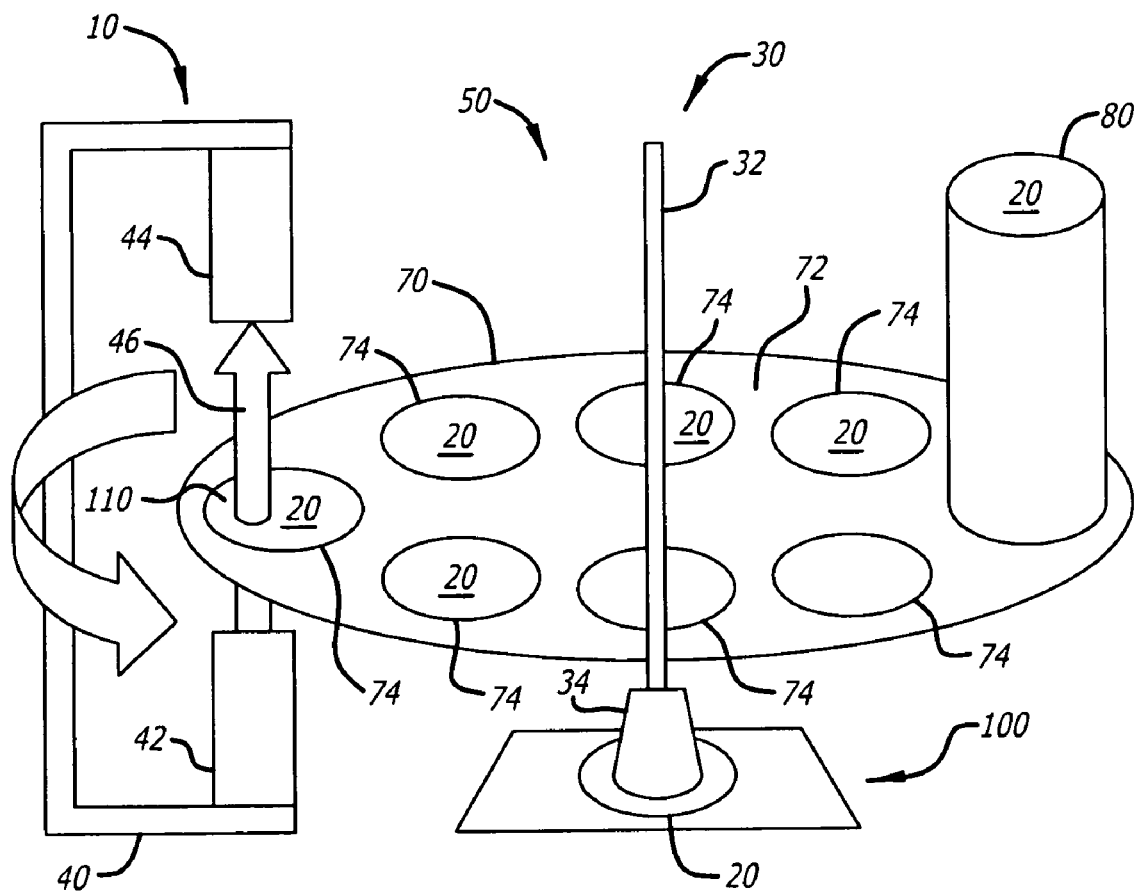
FIG. 8 is a front elevation of a microscope slide coverslip detection station, coverslip station, and coverslip storage unit according to another embodiment of the present invention.

The coverslip detection station 10 may be fixed relative to the transfer mechanism 30 and the number of coverslips 20, or movable relative to the transfer mechanism 30 and the number of coverslips 20, to position the light source 42 and light detector 44 adjacent to the number of coverslips 20. In addition, one or both of the light source 42 and light detector 44 may be independently movable relative to the coverslip detection station 10 and to one another. Suitable drives and controllers may be provided to control movement of the coverslip detection station 10, light source 42, and/or light detector 42. It will be understood that the coverslip detection station 10 may be capable of determining the distance between the light source 42 and light detector 44 in the instance of the light source 42 and light detector 44 being movable relative to one another and the coverslip detection station 10. Alternatively, the light source 42 and light detector 44 may be fixed at a known distance from one another. In either instance, the light source 42 directs light, such as ultraviolet light, through at least a portion of the coverslip testing region. The light may be directed through the coverslip testing region at an angle relative to the coverslip detection station and number of coverslips 20, as shown in FIGS. 1-5, or substantially perpendicular to the coverslip detection station 10, as shown in FIG. 8. Any angle at which the light is directed through the coverslip testing region 110 so as to pass through the coverslip testing region and coverslips, if present, may be used so long as the light travels substantially through the thickness of the coverslips when present in the coverslip testing region.

In one embodiment, the coverslip detection station 10 is provided as a stand-alone device. In another embodiment, a coverslip detection station is provided in an automated slide staining system, which prepares, for example, biological samples for testing. In a further embodiment, the coverslip detection station is provided in an automated analyzer, which conducts automated diagnostic analysis. Examples of automated diagnostic analysis include testing sample biological specimens to check for the presence of an item of interest, which item may be or include all or portions of DNA, RNA, or fragments thereof, complements, peptides, polypeptides, enzymes, prions, proteins, messenger RNA, transfer RNA, mitochondrial RNA or DNA, antibodies, antigens, allergens, parts of biological entities, such as cells, viruses or the like, surface proteins, or functional equivalents of any of the above. Examples of biological specimens include human cells, tissue or bodily fluids, including, but not limited to, serum, red blood cells, white blood cells, whole blood, urine, swabs, plasma, cerebrospinal fluid, lymph fluids, cells and tissue. Moreover, it will be understood that the coverslip detection station 10 is not limited for use with biological samples, and may be readily used to detect the presence of a number of microscope slide coverslips for any application that utilizes coverslips that are transparent to light, such as ultraviolet light. For example, the invention can be used with coverslips for microscope slides carrying non-biological samples, such as inorganic compounds or substances, and other non-biological sample testing as known by those of ordinary skill in the art.

Figure 3:
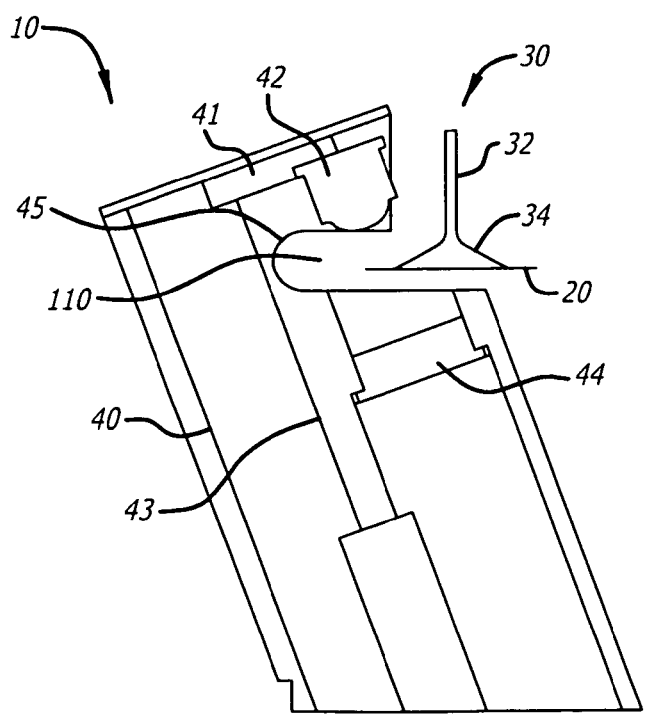
FIG. 3 is the cross-section as shown in FIG. 2, along with a transfer mechanism.
Figure 4:
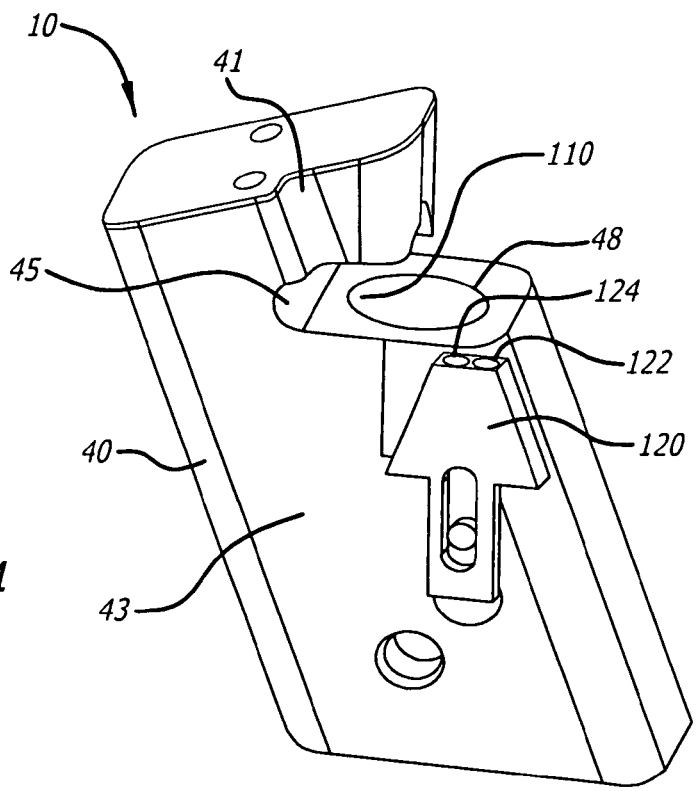
FIG. 4 is an isometric view of a coverslip detection station according to a further embodiment of the present invention.
Figure 5:
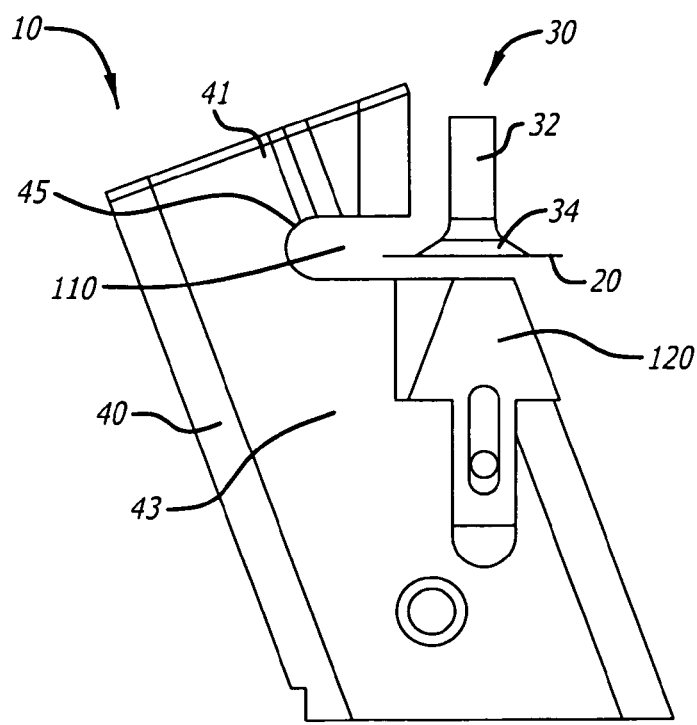
FIG. 5 is a side elevation view of the coverslip detection station shown in FIG. 4, along with a transfer mechanism.
Figure 6:
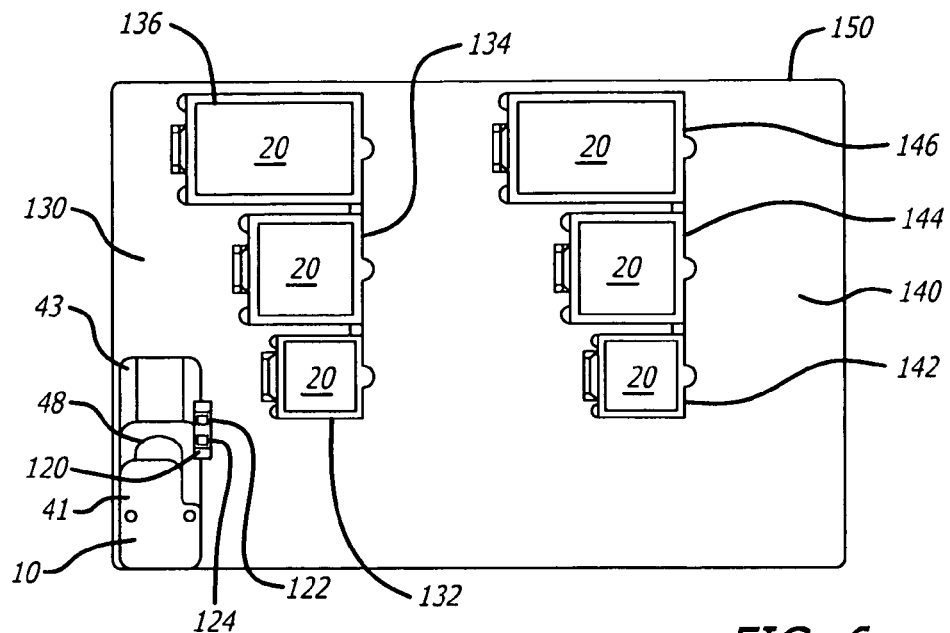
FIG. 6 is a top plan view of coverslip detection station and coverslip storage platform according to one embodiment of the present invention.
Figure 7:
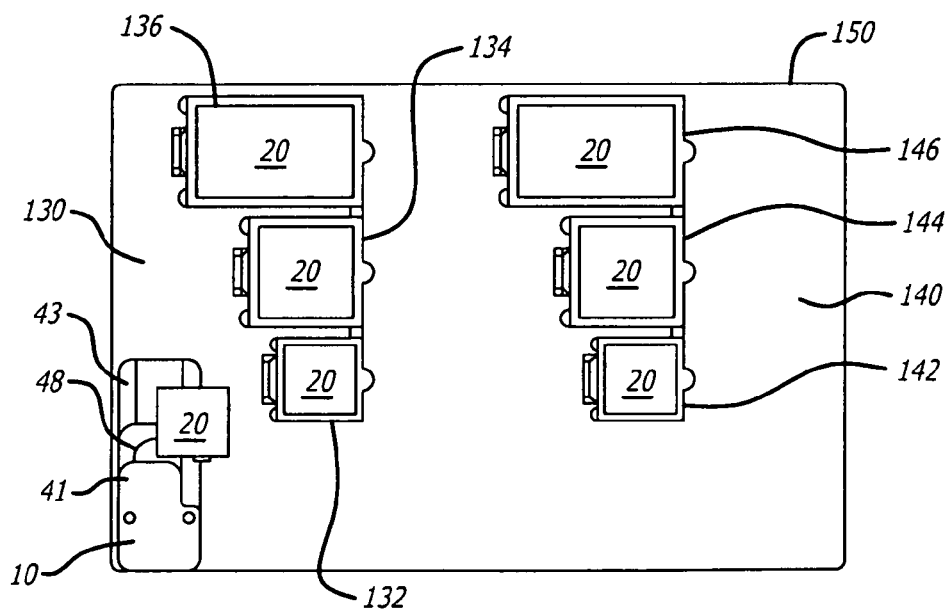
FIG. 7 is a top plan view as described in FIG. 6 with a coverslip located in proximity to the detection station.

As shown in FIGS. 1, 3, and 5, a transfer mechanism 30 positions a number of coverslips 20 in proximity with the detection station 10 and coverslip testing region 110. In one embodiment, the coverslips may be removed from a coverslip storage unit or similar device by the transfer mechanism 30. In another embodiment, the transfer mechanism 30 removes coverslips from packaging in which the coverslips were received. An example of a coverslip storage unit configuration is shown in FIGS. 6 and 7 and discussed in more detail below. The transfer mechanism may be any suitable device for removing, holding, and transferring coverslips. As shown in FIGS. 1, 3, 5 and 8, the transfer mechanism 30 includes a movable arm 32 having a suction cup 34 attached to an end of the arm 32. The arm 32 may be capable of movement along the x, y, and z axes, a combination of two of the three axes, or a single axis. A suitable drive and controller may be provided to control movement of the transfer mechanism 30.

In one embodiment, an automated slide staining system expects a single microscope slide coverslip to be applied to a microscope slide during processing and preparation of a sample placed on the microscope slide. For example, before hybridization a coverslip may be applied to the slide to protect the sample from evaporation and oxidation. In addition, the coverslip protects the sample placed on the microscope slide from debris or other contaminants as the microscope slide is transferred throughout the slide staining system. Once placed on the microscope slide, the coverslip may be removed from the slide to allow further processing and preparation of the sample. Thereafter, a coverslip may be placed again on the microscope slide before the sample is analyzed, for example, at the end of processing a coverslip may be applied to seal the prepared sample for evaluation on a microscope or other analytical device. It will be appreciated that any number of processing steps may be conducted on the sample on the microscope slide, such that coverslips may be applied to and removed from the microscope slide several times during processing and evaluation or analysis of the sample.

To discern the number of coverslips and distinguish therebetween, the transfer mechanism 30 retrieves a number of coverslips 20 from a coverslip storage unit or similar device, which may include zero coverslips, one coverslip, or a plurality of coverslips. One example of a configuration of coverslip storage units is shown in FIGS. 6 and 7. As shown, a coverslip storage platform 150 includes coverslip storage banks 130, 140. Each coverslip storage bank 130, 140 includes coverslip storage units 132, 134, 136 and 142, 144, 146, respectively. The coverslip storage units are configured to store different sizes of coverslips, and have open tops to allow the transfer mechanism to retrieve coverslips from the storage units. For example, the coverslip storage units 132, 142 are open to show a particular size of coverslip 20 stored therein, for example 18 mm×18 mm coverslips. Coverslip storage units 134, 136 are shown having another size of coverslips stored therein, for example 25 mm×25 mm coverslips. The coverslip storage units 144, 146 store yet another dimension of coverslip, for example 25 mm×40mm. The coverslip banks 130, 140 may be configured to store any quantity, size, or number of different types of coverslips.

Because coverslips have a tendency to stick together, a plurality of coverslips may have been retrieved by the transfer mechanism 30 from a coverslip storage unit. In addition, perhaps no coverslips were retrieved by the transfer mechanism 30. The transfer mechanism 30 then transfers the number of coverslips 20 held thereon to the coverslip detection station 10. In one example, to transfer the number of coverslips 20 to the coverslip detection station from a coverslip storage unit, the transfer mechanism 30 retrieves a number of coverslips 20 from a coverslip storage unit through z-axis movement of the transfer mechanism 30. Once the transfer mechanism 30 engages the coverslip 20 for transport, the transfer mechanism returns to its default vertical (z) position. The coverslip testing region 110 is configured to be at the same vertical position as the default vertical position of the transport mechanism 30. As a result, the transfer mechanism is configured to quickly and efficiently position the number of coverslips 20 in the coverslip testing region 110 through horizontal movement along a single plane, which simplifies the programming associated with movement of the transfer mechanism. In addition, movement along a single plane does not hinder the throughput of the detection station and prevents the discernment of the number of coverslips at the coverslip detection station from creating a "bottleneck" or impairment on the throughput and processing of the automated slide staining system.

Once the number of coverslips are placed by the coverslip transfer mechanism 30 in the coverslip testing region 110, the number of coverslips will reside adjacent to the light source 42 and light detector 44 (see FIGS. 1, 3, 5, 7, and 8). In one example, the coverslip transfer mechanism 30 holds the number of coverslips via suction cup 34 during detection (see FIGS. 1, 3, 5; the transfer mechanism is not shown in FIG. 7). At the detection station 10, the number of coverslips are evaluated to discern the actual number of coverslips present in the coverslip testing region. The light source 42 and light detector 44 are positioned so that light, such as ultraviolet light, directed toward the coverslip testing region 110 by the light source 42 is received by the light detector 44. The light source 42 directs the light through at least a portion of the coverslip testing region 110 and number of coverslips 20 when present in the coverslip testing region. As shown in FIGS. 1, 3 and 5, the light, such as ultraviolet light, may be directed toward and through at least a portion of the coverslip testing region 110 and the number of coverslips 20 at an angle relative to the testing region 110 and coverslips 20. The angled position of the light source 42 and light detector 44 allows the transfer mechanism 30 bring the coverslips into proximity with the light source and detector and hold the number of coverslips 20 while the detection station 10 discerns the number of coverslips present in the coverslip testing region 110. In addition, the angled position of the light source 42 and light detector 42 avoids the area of the coverslips covered by the suction cup 34 as the cup 34 would block or otherwise interfere with the light traveling from the light source and through the coverslip testing region to the light detector. As discussed above, it will be appreciated that any angle at which the light is directed through the coverslip testing region 110 and coverslips 20 when present in the coverslip testing region may be used so long as the light travels substantially through the thickness of the coverslips when present in the testing region.

The light, such as ultraviolet light, directed through the coverslip testing region 110 is detected by the light detector 44. The amount of light reaching the light detector 44 is measured through suitable programming and hardware included in the coverslip detection station 10. The coverslip detection station 10 then compares the measured amount with an amount of light that would result when no coverslips are present at the coverslip detection station, for example, a calibration amount. The measured amount indicates the number of coverslips residing within the coverslip testing region 110. The measured amount may discern between zero coverslips, one coverslips, and a plurality of coverslips present in the testing region 110 of the detection station 10. It will be understood that the detection station 10 may include a suitable analog to digital converter or digital to analog converter, and/or microprocessor and associated electronics, or similar devices to compare and calculate the measured amounts with the calibration amount. The microprocessor or similar device(s) is capable of determining whether zero, one, or a plurality of coverslips have been presented in the testing region 110 based on the amount of light passing through the coverslip testing region 110.

Once the coverslip detection station 10 discerns the number of coverslips that have been presented to the station, the transfer mechanism 30 or other similar device applies a single coverslip to a microscope slide, moves back to the coverslip storage unit and reattempts to engage a coverslip in the event no coverslips were retrieved by the transfer mechanism 30, or disposes of the plurality of coverslips. After disposal of a plurality of coverslips, the transfer mechanism 30 again engages and removes a number of coverslips from the coverslip storage unit. Thereafter, the number of coverslips are transferred to the coverslip detection station 10 to discern the number of coverslips removed from the coverslip storage unit as described above. The process is repeated until a single coverslip is removed and detected by the detection station 10. After a predetermined number of attempts and failures to remove and detect a single coverslip, a warning signal or failure signal may be triggered to notify an operator that the transfer mechanism and/or the detection station needs maintenance.

In one example, as shown in FIGS. 4-7, the coverslip detection station includes a proximity sensor 120 comprised of a light source 122 and a light detector 124. The proximity sensor is attached to the outside of the lower portion 43 of body 40. The proximity sensor is positioned adjacent to the coverslip testing region 110. In operation, the proximity sensor detects whether a coverslip is actually present in the coverslip testing region 110. The light source 122 emits lights toward the coverslip testing region 110 and the light source detects an amount of light reflected from the coverslip testing region 110 to determine whether a coverslip is present in the testing region 110. The proximity sensor 120 also allows the light source 42 to be turned off intermittently between testing of coverslips to prevent the light source 42 from being constantly powered on even during instances when the transfer mechanism is not attempting to position a coverslip at the detection station. As a result, the light source 42 is preserved and prevented from "burning-out" prematurely. Once the proximity sensor detects that a coverslip is present in the coverslip testing region 110, the light source 122 is powered off so as to not interfere with the coverslip detection. In addition, the light source 42 is powered on to begin the discernment of the number of coverslips in the testing region. When the proximity sensor detects that no coverslip is present in the coverslip testing region 110, the transfer mechanism 30 moves back to the coverslip storage unit to reattempt to engage a coverslip. In this example, the light source 42 remains off until a coverslip is detected by the proximity sensor 120 to be in the coverslip testing region 110, thus preserving the light source 42 and preventing premature burning out of the light source 42.

Turning to FIG. 8, a detection station 10, a coverslip station 50, a transfer mechanism 30, and a coverslip storage unit 80 according to another embodiment are shown. As shown in FIG. 8, the coverslip station 50 is positioned adjacent to the detection station 10. The detection station 10 may be fixed relative to the coverslip station 50, or movable relative to the coverslip station 50 to position the light source 42 and light detector 44 in proximity to the coverslip station 50 and a number of coverslips held thereon. A suitable drive and controller may be provided to control movement of the detection station 10, coverslip station 50, and transfer mechanism 30.

The coverslip station 50 includes a coverslip stage 70 for holding a number of coverslips 20. The coverslip stage 70 comprises a carousel 72 for holding and positioning a number of coverslips 20 into proximity with the light source 42 and light detector 44 of detection station 10 and coverslip testing region 110. A suitable drive and controller may be provided to control movement of the carousel 72 with respect to the light source 42 and light detector 44. The coverslips 20 are held on the carousel 72 by a holder 74. As shown in FIG. 8, several holders 74 are positioned around the circumference of carousel 72. Each holder 74 may include a suitable structure for holding a coverslip. For example, holders 74 may include a suction device for holding the coverslips thereon during positioning and detection. In another embodiment, the holders 74 may include clips, clamps, or other structure to secure the coverslips on the stage 30. In a further embodiment, the holders may comprise an indent, impression, or shelf for receiving a coverslip. Although several holders 74 are shown in FIG. 8, the invention contemplates any number of holders for use with the coverslip stage 70. It will be understood that the holders 74 include openings or transparent portions to allow light generated by the light source 42 to pass through the holders 74 and any coverslip held thereon. Alternatively, it will be understood that the surface area of the holders 74 may be smaller than the surface area of the coverslip, for example in the form of a pedestal, which allows light to pass through an edge portion of a coverslip held thereon without light having to pass through the coverslip stage.

Other suitable structures may be utilized as the coverslip stage 70, such as, for example, the coverslip stage may be fixed relative to the light source 42 and light detector 44 so that the light source and detector move relative to the stage 70. In another embodiment, the coverslip stage may be movable relative to the light source 42 and light detector 44 along the x, y, and z axes, any combination of two axes, or a single axis, to position coverslips in proximity with the light source 42 and light detector 44. A suitable drive and controller may be provided to control movement of the coverslip stage.

Microscope slide coverslips may be provided in a coverslip storage unit 80, as shown in FIG. 8, or in the coverslip storage banks shown in FIGS. 6 and 7, or other similar devices for storing coverslips. The coverslip storage unit 80 and storage banks 130, 140 may be provided as a stand-alone unit, or as a component of the detection station 10, the coverslip station 50, automated slide staining apparatus, automated analyzer, or similar device. The coverslips may be loaded either manually or automatically into the coverslip storage units. Alternatively, coverslips may be provided from the packaging in which they are received. The storage units may be fixed relative to the detection device 10, coverslip station 50, or may be movable to and from the coverslip station 50. In example, the storage unit 80 may dispense coverslips 20 onto the holders 74 of carousel 72. Any suitable device may be provided to dispense coverslips to the holders 74, such as, for example, a pusher arm or a reciprocating pin or pins, which protrude from unit 80 and retract back to unit 80 to dispense coverslips through the bottom of unit 80. The transfer mechanism 30 may also retrieve a number of coverslips 20 from the storage unit 80 and position the coverslips 20 on holders 74, as described above, for example, with respect to FIGS. 6 and 7. Suitable drives and controllers may be provided to control movement of the storage unit 80 and dispensing of coverslips onto carousel 72.

As shown in FIG. 8, the coverslip station moves to position a number of coverslips 20 received from the storage unit 80 to a position adjacent to the detection station 10. The coverslip transfer mechanism 30 may deposit the coverslips on the coverslip stage 70 or the storage unit 80 may dispense the coverslips directly to the coverslip stage 70 as described above. In particular, carousel 72 selectively and incrementally rotates to position the holders 74 in a position to receive coverslips from the storage unit 80 and/or the transfer mechanism 30. Once the coverslips are deposited into the holders 74, the carousel 72 rotates to position the number of coverslips at the detection station 10. At the detection station, the coverslip stage 70 moves the coverslips 20 in proximity with the light source 42 and light detector 44 and positions the number of coverslips in the coverslip testing region 110.

Once positioned at the detection station 10 in the coverslip testing region 110, the number of coverslips are interrogated to discern the number of coverslip present in the coverslip testing region, in the manner described above. The light source 42 and light detector 44 are positioned so that light, such as ultraviolet light, directed by the light source 42 toward and through at least a portion of the testing region 110 is received by the light detector 44. The light source 42 also directs the light through at least a portion of a number of coverslips 20 when present on the holder 74. As shown in FIG. 8, the light may be directed through the coverslip testing region in a direction substantially perpendicular to the testing region and coverslips. It will be appreciated that any angle at which the light is directed through the testing region and the coverslips when present may be used so long as the light travels substantially through the thickness of the coverslips as described above. Thereafter, the detection station 10 determines whether zero, one, or a plurality coverslips are present in the testing region, in the manner previously described.

After the coverslip detection station 10 determines the number of coverslips that have been presented to the detection station 10 in the coverslip testing region 110, the carousel 72 rotates to position the holder 74 out of proximity from the detection station 10. The transfer mechanism 30 or other similar device then applies the single coverslip to a microscope slide 100, as shown in FIG. 8, disposes of the plurality of coverslips, or in the event no coverslips were retrieved by the transfer mechanism 30, the transfer mechanism moves back to the coverslip storage unit and reattempts to engage a coverslip. Thereafter, a number of coverslips on the next holder 74 are already positioned at the detection station 10 as a result of the carousel 72 rotating the previous holder 74 away from the detection station. In this manner, whether no coverslips are detected, a single coverslip is detected and applied to a microscope slide, or a plurality of coverslips are detected and disposed, the next holder 74 carrying a number of coverslips is ready for detection. Thus, the coverslip station 50 continuously positions coverslips at the detection station, which increases throughput of coverslip detection and application to microscope slides. Upon detection of a plurality of coverslips, the detection process is repeated, in the manner described above, until a single coverslip is detected by the detection station 10. After a predetermined number of attempts and failures to remove and detect a single coverslip, a warning signal or failure signal may be triggered to notify that the transfer mechanism needs maintenance.

In another embodiment, the detection station moves to retrieve a number of coverslips. The coverslips may be dispensed onto the detection station, or the detection station may include a mechanism for retrieving the coverslips, such as an arm or other suitable device, for retrieving the coverslips. In a further embodiment, the transfer mechanism may move the coverslips and the detection station may also be movable to bring the detection station and coverslips to a position adjacent one another. In either embodiment, the detection station determines the number of coverslips that have been presented to the detection station, in the manner described above.

In the present invention, sophisticated and precise alignment and positioning of the coverslips at the coverslip detection station or adjacent the light source and detector is minimized due to the flexibility of the invention to measure a reduction in light passing through a coverslip or plurality of coverslips. An accurate measurement results from the coverslips being positioned such that light from the light source passes through at least a portion of the coverslip which is received by the light detector.

Calibration of the light source and light detector is not burdensome and can be carried out anytime a coverslip is not present at the coverslip detection station. This allows for one time calibration of the light source and light detector as well as a way to continuously calibrate the light source and light detector if necessary. In one example, the light source and light detector are automatically calibrated using a dark calibration and a light calibration, in which no coverslips are present in the coverslip testing region for either calibration. In dark calibration, the light source does not produce any light and the detector detects any background light to account for "noise" or background light. The dark calibration may be conducted periodically at predetermined intervals. Subsequently, light calibration is conducted in which the light source produces light incrementally until an optimum intensity is generated by the light source and detected by the light detector, which falls within a predetermined range. The light calibration is accomplished by varying the current levels supplied to the light source to ensure that the light detector is detecting the correct amount of light. Once the optimal intensity of light is generated by the light source, such that the correct amount of light is detected by the light detector, that amount of measured light is designated as the calibration amount, which corresponds to the amount of light detected when no coverslips are present in the coverslip testing region. This calibration amount is used in subsequent measurements and computations of light absorption to discern the number of coverslips present in the coverslip testing region. After the number of coverslips have been discerned and moved away, from the coverslip testing region, the light source may be triggered again to generate light which is measured and compared with the calibration amount to ensure the calibration amount used for coverslip detection is correct.

Use of absorption of light, such as absorption of ultraviolet light, for detection and calibration discussed above protects against factors of aging of the light source, buildup of debris, such as dirt, and corrosion. The light produced by the light source may be calibrated as described above, by adjusting the light source to produce the optimal amount of light which is detected by the light detector. This calibrated measurement compensates for factors such as aging of the light source, buildup of debris, or corrosion because the optimal intensity may be adjusted, and moreover, the amount of light absorbed by each coverslip remains substantially constant even when the amount of light directed through coverslips changes. A measurable difference will still exist even in the case of light source aging, buildup of debris, or corrosion which reduces the amount of light emitted from the light source. In addition, other advantages may be apparent to one of ordinary skill in the art in view of the disclosure herein.

EXAMPLE

A UVTOP® ultraviolet light-emitting diode (LED), Model No. UVTOP310TO39BL having peak wavelengths in the range of about 310 to about 320 nanometers, manufactured by Sensor Electronic Technology, Inc., was utilized as the ultraviolet light source. A quartz windowed UV sensitive photodiode, Model No. S1226-8BQ, manufactured by Hamamatsu Photonics K.K, was utilized as the ultraviolet detector. 18 mm×18 mm, 25 mm×25 mm, and 40 mm×25 mm glass coverslips were used in which double coverslips were prepared by gluing two coverslips together at their center. Single and double coverslips were placed together in a coverslip storage unit. A transfer arm having a suction cup on one end was used to engage the coverslips and transport them into proximity with the light source and light detector and into a coverslip testing region formed between the light source and light detector. Ultraviolet light generated by the ultraviolet LED was directed through the coverslip testing region and coverslips present therein and detected by the photodiode. A total of 280 single coverslips were interrogated with ultraviolet light as described above, in which 120 were 18 mm×18 mm coverslips, 120 were 25 mm×25 mm coverslips, and 40 were 25 mm×40 mm coverslips. Additionally, a total of 145 double coverslips were interrogated with ultraviolet light as described above, in which 50 were 18 mm×18 mm coverslips, 77 were 25 mm×25 mm coverslips, and 18 were 25 mm×40 mm coverslips. The measurements of ultraviolet light in terms of absorbance were linearized using the Beer-Lambert law and output in actual optical density units. The absorbance measurements were linearized by taking the natural log of the calibration reading (i.e., zero coverslips) and dividing the calibration reading by the actual reading when one or two coverslips were present according to the following formula: ln (calibration amount/actual measured amount). The mean absorbance measurement for single coverslips was 0.72 with a standard deviation of 0.03. For two or double coverslips, the mean absorbance measurement was 1.23 with a standard deviation of 0.04. As the results indicate, a clear distinction in measured absorbance exists between single and double coverslips. Therefore, the present disclosure provides an accurate method and apparatus for discerning between zero, one, and a plurality of microscope slide coverslips.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments and examples could be provided in any combination with the other embodiments and examples disclosed herein.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A method of discerning a number of microscope slide coverslips in an automated microscope slide staining system comprising:
    directing light toward a coverslip testing region, wherein the light is directed to pass through at least a portion of the coverslip testing region; and
    discerning the number of coverslips in the coverslip testing region based on the amount of light passing through the coverslip testing region, wherein the discerning step comprises measuring a reduction of the light passing through the coverslip testing region.

2. The method of claim 1, wherein the light is ultraviolet light.

3. The method of claim 2, wherein the ultraviolet light is at a wavelength of between about 200 nanometers and about 400 nanometers.

4. The method of claim 2 wherein the ultraviolet light is at a wavelength of between about 310 and about 320 nanometers.

5. The method of claim 4, wherein the amount of ultraviolet light passing through a single coverslip in the coverslip testing region is between about 40 percent and about 45 percent of the ultraviolet light directed toward the coverslip testing region.

6. The method of claim 4, wherein the amount of ultraviolet light passing through two coverslips in the coverslip testing region is between about 20 percent and about 25 percent of the ultraviolet light directed toward the coverslip testing region.

7. The method of claim 1, further comprising:
    bringing a number of coverslips into proximity with a coverslip detection station, the coverslip detection station comprising an ultraviolet light source and an ultraviolet light detector, wherein the number of coverslips is placed in the coverslip testing region between the ultraviolet light source and the ultraviolet light detector; and
    wherein the step of directing light comprises directing ultraviolet light from the ultraviolet light source toward the ultraviolet light detector in a path that travels through at least a portion of the coverslip testing region.

8. The method of claim 7, further comprising:
    directing light from a light source toward the coverslip testing region; and
    determining the presence or absence of the number of coverslips in the coverslip testing region based on an amount of light reflected from the coverslip testing region and received by a light detector.

9. An apparatus for automatically discerning a number of coverslips comprising:
    an ultraviolet light source for producing ultraviolet light;
    an ultraviolet light detector for detecting ultraviolet light from the ultraviolet light source; and
    a transfer mechanism for bringing the number of coverslips into proximity with the ultraviolet light source and the ultraviolet light detector, wherein the ultraviolet light source is configured to direct ultraviolet light through at least a portion of a coverslip testing region and the ultraviolet detector is configured to detect ultraviolet light passing through the coverslip testing region to discern the number of coverslips in the coverslip testing region.

10. The apparatus of claim 9, wherein the transfer mechanism is configured to bring the number of coverslips into the coverslip testing region between the ultraviolet light source and the ultraviolet detector by movement through a single plane extending between the ultraviolet light source and the ultraviolet light detector.

11. The apparatus of claim 9, wherein the ultraviolet light source comprises a light-emitting diode and the ultraviolet light detector comprises a photodiode.

12. The apparatus of claim 9, further comprising:
    a light source configured to direct light toward the coverslip testing region;
    a light detector configured to detect light from the light source reflected from the coverslip testing region for determining the presence or absence of the number of coverslips in the coverslip testing region.

13. An apparatus for automatically discerning a number of microscope slide coverslips in an automated slide staining system comprising:
    a coverslip detection station for discerning a number of coverslips, wherein the coverslip detection station is configured to direct ultraviolet light to pass through at least a portion of a coverslip testing region and to discern the number of coverslips in the coverslip testing region based on the amount of ultraviolet light passing through the coverslip testing region, wherein the coverslip detection station measures the reduction in transmission of ultraviolet light passing through the coverslip testing region to discern the number of coverslips in the coverslip testing region.

14. The apparatus of claim 13, wherein the coverslip detection station comprises an ultraviolet light source and an ultraviolet detector.

15. The apparatus of claim 14, further comprising a transfer mechanism for bringing the number of coverslips into proximity with the coverslip detection station.

16. The apparatus of claim 15, wherein the transfer mechanism is configured to bring the number of coverslips into the coverslip testing region between the ultraviolet light source and the ultraviolet detector by movement through a single plane extending between the ultraviolet light source and the ultraviolet detector.

17. The apparatus of claim 14, wherein the ultraviolet light source comprises a light-emitting diode and the ultraviolet detector comprises a photodiode.

18. The apparatus of claim 13, further comprising:
    a light source configured to direct light toward the coverslip testing region;
    a light detector configured to detect light from the light source reflected from the coverslip testing region for determining the presence or absence of the number of coverslips in the coverslip testing region.

19. A method of discerning a number of microscope slide coverslips in an automated microscope slide staining system comprising:
    bringing a number of coverslips into proximity with a coverslip detection station, the coverslip detection station comprising an ultraviolet light source and an ultraviolet light detector, wherein the number of coverslips is placed in a coverslip testing region between the ultraviolet light source and the ultraviolet light detector;
    directing ultraviolet light from the ultraviolet light source toward the ultraviolet light detector in a path that travels through at least a portion of the coverslip testing region; and
    discerning the number of coverslips in the coverslip testing region based on the amount of ultraviolet light passing through the coverslip testing region.

20. The method of claim 19, further comprising:
    directing light from a light source toward the coverslip testing region; and
    determining the presence or absence of the number of coverslips in the coverslip testing region based on an amount of light reflected from the coverslip testing region and received by a light detector.

21. An apparatus for automatically discerning a number of microscope slide coverslips in an automated slide staining system comprising:
- a coverslip detection station for discerning a number of coverslips, wherein the coverslip detection station is configured to direct ultraviolet light to pass through at least a portion of a coverslip testing region and to discern the number of coverslips in the coverslip testing region based on the amount of ultraviolet light passing through the coverslip testing region, the coverslip detection station comprising an ultraviolet light source and an ultraviolet detector;
- a transfer mechanism for bringing the number of coverslips into proximity with the coverslip detection station, wherein the transfer mechanism is configured to bring the number of coverslips into the coverslip testing region between the ultraviolet light source and the ultraviolet detector by movement through a single plane extending between the ultraviolet light source and the ultraviolet detector.

* * * * *